(12) United States Patent
Arya et al.

(10) Patent No.: US 10,098,690 B2
(45) Date of Patent: Oct. 16, 2018

(54) INSTRUMENTS, SYSTEMS, AND METHODS FOR SEALING TISSUE STRUCTURES

(71) Applicant: COVIDIEN LP, Mansfield, MA (US)

(72) Inventors: Shobhit Arya, Berkshire (GB); Lei Su, London (GB); Ara W. Darzi, London (GB); George B. Hanna, Middlesex (GB)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/907,449

(22) Filed: Feb. 28, 2018

(65) Prior Publication Data

US 2018/0185088 A1 Jul. 5, 2018

Related U.S. Application Data

(63) Continuation of application No. 15/200,176, filed on Jul. 1, 2016, now Pat. No. 9,924,999, which is a
(Continued)

(51) Int. Cl.
*A61B 18/14* (2006.01)
*A61B 18/00* (2006.01)
(Continued)

(52) U.S. Cl.
CPC ............. *A61B 18/1445* (2013.01); *A61B 2017/00057* (2013.01); *A61B 2018/0063* (2013.01);
(Continued)

(58) Field of Classification Search
CPC ............ A61B 18/1442; A61B 18/1445; A61B 18/085; A61B 2018/00494;
(Continued)

(56) References Cited

U.S. PATENT DOCUMENTS

| D249,549 S | 9/1978 | Pike |
|---|---|---|
| D263,020 S | 2/1982 | Rau, III |

(Continued)

FOREIGN PATENT DOCUMENTS

| CN | 201299462 Y | 9/2009 |
|---|---|---|
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Thomas Giuliani

(57) ABSTRACT

A method of sealing bowel tissue includes grasping bowel tissue between first and second electrically-conductive surfaces, applying a clamping pressure to the grasped bowel tissue in a range of about 1 kg/cm² to about 2.5 kg/cm², supplying energy to at least one of the first and second electrically-conductive surfaces such that the energy is conducted between the first and second electrically-conductive surfaces and through the grasped bowel tissue to seal the grasped bowel tissue, and monitoring one or more parameters during the supplying of energy to the electrically-conductive surface(s). Instruments, end effector assemblies, generators, and systems suitable for this purpose are also provided.

9 Claims, 5 Drawing Sheets

Related U.S. Application Data continuation of application No. 14/017,572, filed on Sep. 4, 2013, now Pat. No. 9,433,461.

(60) Provisional application No. 61/698,270, filed on Sep. 7, 2012.

(51) Int. Cl.
  *A61B 18/12* (2006.01)
  *A61B 17/00* (2006.01)

(52) U.S. Cl.
  CPC .............. *A61B 2018/00494* (2013.01); *A61B 2018/00654* (2013.01); *A61B 2018/00672* (2013.01); *A61B 2018/00678* (2013.01); *A61B 2018/00702* (2013.01); *A61B 2018/00714* (2013.01); *A61B 2018/00755* (2013.01); *A61B 2018/00791* (2013.01); *A61B 2018/00875* (2013.01); *A61B 2018/126* (2013.01); *A61B 2018/1253* (2013.01)

(58) Field of Classification Search
  CPC .. A61B 2018/0063; A61B 2018/00607; A61B 2018/00589; A61B 2018/00636; A61B 2018/00642; A61B 2018/00666; A61B 2018/00672; A61B 2018/00678; A61B 2018/00702; A61B 2018/00708; A61B 2018/00791; A61B 2018/126; A61B 2018/00875; A61B 2018/00898; A61B 2018/00755; A61B 2018/00714
  USPC .............................. 606/37, 38, 41, 42, 50–52
  See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,443,463 A | 8/1995 | Stern et al. |
| D384,413 S | 9/1997 | Zlock et al. |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,123,701 A | 9/2000 | Nezhat |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,676,660 B2 | 1/2004 | Wampler et al. |
| 6,702,810 B2 | 3/2004 | McClurken et al. |
| D493,888 S | 8/2004 | Reschke |
| 6,775,575 B2 | 8/2004 | Bommannan et al. |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,953,461 B2 | 10/2005 | McClurken et al. |
| D525,361 S | 7/2006 | Hushka |
| D531,311 S | 10/2006 | Guerra et al. |
| 7,115,139 B2 | 10/2006 | McClurken et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,909,820 B2 | 3/2011 | Lipson et al. |
| 7,976,544 B2 | 7/2011 | McClurken et al. |
| D649,249 S | 11/2011 | Guerra |
| D649,643 S | 11/2011 | Allen, IV et al. |
| 8,128,624 B2 | 3/2012 | Couture et al. |
| D661,394 S | 6/2012 | Romero et al. |
| 8,192,444 B2 | 6/2012 | Dycus |
| 8,382,754 B2 | 2/2013 | Odom et al. |
| 8,679,140 B2 | 3/2014 | Butcher |
| RE44,834 E | 4/2014 | Dumbauld et al. |
| 8,777,945 B2 | 7/2014 | Floume et al. |
| 8,968,311 B2 | 3/2015 | Allen, IV et al. |
| 9,433,461 B2 | 9/2016 | Arya et al. |
| 2004/0162596 A1 | 8/2004 | Altshuler et al. |
| 2005/0033278 A1 | 2/2005 | McClurken et al. |
| 2006/0052779 A1* | 3/2006 | Hammill ............ A61B 18/1442 606/51 |
| 2006/0217709 A1 | 9/2006 | Couture et al. |
| 2008/0172048 A1 | 7/2008 | Martin et al. |
| 2009/0018535 A1 | 1/2009 | Schechter et al. |
| 2009/0204114 A1 | 8/2009 | Odom |
| 2010/0217258 A1* | 8/2010 | Floume ................ A61B 5/0059 606/34 |
| 2011/0144635 A1* | 6/2011 | Harper ............... A61B 18/1206 606/34 |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0005667 A1 | 1/2014 | Stulen et al. |
| 2014/0025052 A1 | 1/2014 | Nau, Jr. et al. |
| 2014/0025053 A1 | 1/2014 | Nau, Jr. et al. |

(56) References Cited

U.S. PATENT DOCUMENTS

| | | |
|---|---|---|
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009318 U1 | 8/2007 |
| DE | 202007009317 U1 | 10/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1159926 A3 | 3/2003 |
| JP | 61501068 | 9/1984 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | H0856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | 10155798 A | 6/1998 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A3 | 4/2006 |
| WO | 2008040483 A1 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: Chandler.
U.S. Appl. No. 09/177,950, filed Oct. 23, 1998; inventor: Frazie.
U.S. Appl. No. 09/387,883, filed Sep. 1, 1999; inventor: Schmaltz.
U.S. Appl. No. 09/591,328, filed Jun. 9, 2000; inventor: Ryan.
U.S. Appl. No. 12/336,970, filed Dec. 17, 2008; inventor: Sremcich.
U.S. Appl. No. 13/731,674, filed Dec. 31, 2012; inventor: Siebrecht.

\* cited by examiner

INSTRUMENTS, SYSTEMS, AND METHODS FOR SEALING TISSUE STRUCTURES

CROSS-REFERENCE TO RELATED APPLICATIONS

This application is a continuation application of U.S. patent application Ser. No. 15/200,176, filed on Jul. 1, 2016, now U.S. Pat. No. 9,924,999, which is a continuation application of U.S. patent application Ser. No. 14/017,572, filed on Sep. 4, 2013, now U.S. Pat. No. 9,433,461, which claims the benefit of U.S. Provisional Patent Application No. 61/698,270, filed on Sep. 7, 2012, the entire contents of each of which are hereby incorporated by reference herein.

BACKGROUND

Technical Field

The present disclosure relates to surgical instruments, systems, and methods. More particularly, the present disclosure relates to surgical instruments, systems, and methods for sealing tissue structures such as bowel (intestine) tissue or other similar tissue structures.

Description of Related Art

Approximately 2.5 million bowel fusion or anastomosis procedures are performed worldwide each year. Fusion and anastomosis of the bowel has traditionally been accomplished using sutures and/or staples.

Energy-based surgical instruments and systems, as an alternative or in addition to suturing and/or stapling, utilize both mechanical clamping action and energy, e.g., radiofrequency (RF) energy, to affect hemostasis by heating tissue to coagulate and/or cauterize tissue. Certain surgical procedures require more than simply coagulating/cauterizing tissue and rely on the unique combination of clamping pressure, precise energy control, and/or gap distance between sealing surfaces to "seal" tissue. Depending on the particular tissue structure to be sealed, the optimal parameters, e.g., clamping pressure, precise energy control, and/or gap distance, may vary.

SUMMARY

A method of sealing bowel tissue (or other similar tissue structures) provided in accordance with the present disclosure includes grasping bowel tissue between first and second electrically-conductive surfaces, applying a clamping pressure to the grasped bowel tissue in a range of about 1 kg/cm$^2$ to about 2.5 kg/cm$^2$, supplying energy to the first and/or second electrically-conductive surface such that the energy is conducted between the surfaces and through the grasped bowel tissue to seal the grasped bowel tissue, and monitoring one or more parameters during the supplying of energy to the surface(s). The one or more parameters may be bowel tissue temperature, bowel tissue impedance, an optical property of bowel tissue, and/or sealing time.

With regard to bowel tissue temperature, the method may include controlling the supply of energy to the surface(s) to maintain the bowel tissue temperature between a lower temperature limit and an upper temperature limit. More specifically, the lower temperature limit may correspond to the minimum bowel tissue temperature for sealing bowel tissue, while the upper temperature limit may correspond to the maximum bowel tissue temperature prior to occurrence of bowel tissue denaturation, bowel tissue damage, and/or breakdown of bowel tissue layer architecture.

With regard to bowel tissue impedance, the method may include controlling the supply of energy to the surface(s) to maintain a target impedance ramp, e.g., about 0.010 Ω/ms, and/or supplying energy to the surface(s) until bowel tissue impedance reaches a target end impedance, e.g., about 200Ω.

With regard to one or more optical properties of bowel tissue, the method may include supplying energy to the surface(s) until the optical property of bowel tissue indicates bowel tissue denaturation, bowel tissue damage, and/or breakdown of bowel tissue layer architecture.

With regard to sealing time, the method may include supplying energy to the surface(s) for a sealing time of between about 18 and 22 seconds.

Another method of sealing bowel tissue provided in accordance with the present disclosure includes grasping bowel tissue with an applied clamping pressure in a range of about 1 kg/cm$^2$ to about 2.5 kg/cm$^2$, supplying energy to the grasped bowel tissue, and controlling the supply of energy to the grasped bowel tissue such that the grasped bowel tissue is sufficiently sealed with minimal bowel tissue denaturation, bowel tissue damage, and breakdown of bowel tissue layer architecture. Controlling the supply of energy includes monitoring one or more parameters and providing control based on the one or more parameters.

In one aspect of the present disclosure, the parameter is bowel tissue temperature and controlling the supply of energy includes maintaining the bowel tissue temperature between a lower temperature limit, corresponding to the minimum bowel tissue temperature for sealing bowel tissue, and an upper temperature limit, corresponding to the maximum bowel tissue temperature prior to occurrence of at least one of bowel tissue denaturation, bowel tissue damage, and breakdown of bowel tissue layer architecture.

In another aspect of the present disclosure, the parameter is bowel tissue impedance and controlling the supply of energy includes maintaining a target impedance ramp, e.g., about 0.010 Ω/ms, and/or supplying energy until bowel tissue impedance reaches a target end impedance, e.g., about 200Ω.

In still yet another aspect of the present disclosure, the parameter is an optical property of bowel tissue and controlling the supply of energy includes supplying energy until the optical property of bowel tissue indicates bowel tissue denaturation, bowel tissue damage, and/or breakdown of bowel tissue layer architecture.

Also provided in accordance with the present disclosure are instruments, end effector assemblies, generators, and systems suitable for use in accordance with the above-detailed methods.

BRIEF DESCRIPTION OF THE DRAWINGS

Various aspects and features of the present disclosure are described herein with reference to the drawings wherein like reference numerals identify similar or identical elements.

DETAILED DESCRIPTION

Figure 1A:
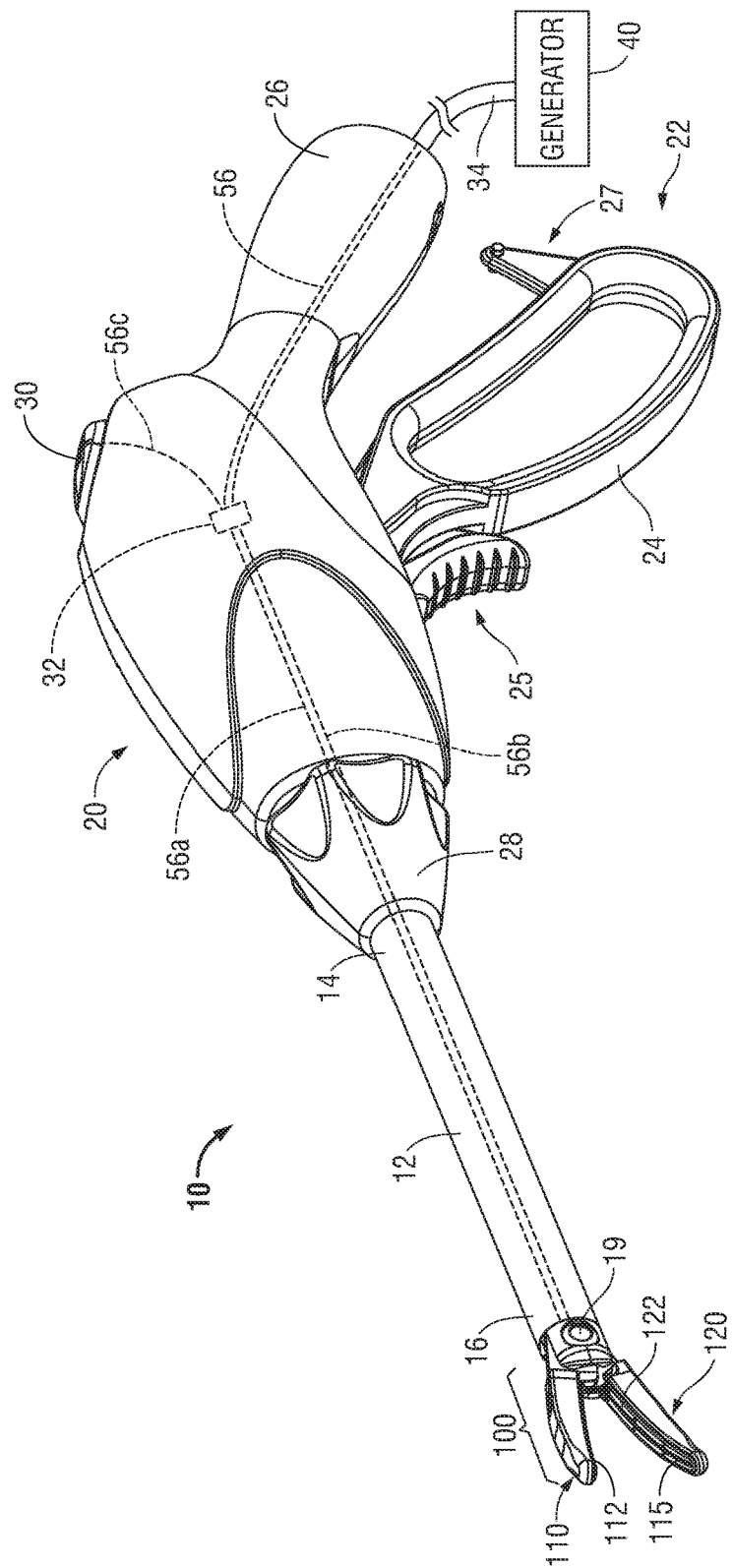
FIG. 1A is a perspective view of a surgical instrument provided in accordance with the present disclosure.

The present disclosure relates generally to surgical devices and methods for applying energy, e.g., RF energy, to bowel (intestine) tissue or other similar tissue structures to treat, e.g., seal, tissue. Referring to FIG. 1A, a surgical forceps 10 is depicted. For the purposes herein, either surgical forceps 10, or any other suitable surgical instrument may be utilized in accordance with the present disclosure. Obviously, different connections and considerations apply to each particular type of instrument; however, the aspects and features of the present disclosure with respect to sealing bowel tissue or other similar tissue structures remains generally consistent with respect to any suitable instrument.

Continuing with reference to FIG. 1A, forceps 10 includes a shaft 12, a housing 20, a handle assembly 22, a trigger assembly 25, a rotating assembly 28, and an end effector assembly 100. Shaft 12 has a distal end 16 configured to mechanically engage end effector assembly 100 and a proximal end 14 that mechanically engages housing 20. A cable 34 couples forceps 10 to an energy source, e.g., an RF generator 40, for transmitting energy and control signals between generator 40 and forceps 10. Cable 34 houses a plurality of wires 56 that are internally divided within handle assembly 22 and/or in shaft 12 into wires 56a-56c, which electrically interconnect end effector assembly 100, activation switch 30, and/or generator 40 with one another. Generator 40 is described in greater detail below.

With continued reference to FIG. 1A, handle assembly 22 includes a movable handle 24 and a fixed handle 26. Fixed handle 26 is integrally associated with housing 20 and movable handle 24 is movable relative to fixed handle 26. Movable handle 24 is ultimately connected to a drive assembly (not shown) that, together, mechanically cooperate to impart movement of jaw members 110, 120 of end effector assembly 100 between a spaced-apart position and an approximated position to grasp tissue therebetween. As shown in FIG. 1A, movable handle 24 is initially spaced-apart from fixed handle 26 and, correspondingly, jaw members 110, 120 are disposed in the spaced-apart position. Movable handle 24 is movable from this initial position to one or more compressed positions corresponding to one or more approximated positions of jaw members 110, 120 (see FIG. 2B). A latching assembly 27 may be provided for selectively locking movable handle 24 relative to fixed handle 26 at various positions between the initial position and the compressed position(s) to lock jaw members 110, 120 at various different positions during pivoting, e.g., the one or more approximated positions. Rotating assembly 28 is rotatable in either direction to similarly rotate end effector assembly 100 relative to shaft 12.

End effector assembly 100 is shown attached at the distal end 16 of shaft 12 and includes opposing jaw members 110 and 120. Each jaw member 110, 120 includes an electrically-conductive tissue-contacting surface 112, 122, respectively, that cooperate to grasp tissue therebetween and seal grasped tissue upon application of energy from generator 40. More specifically, tissue-contacting surfaces 112, 122 are electrically coupled to generator 40, e.g., via wires 56a, 56b, and are configured to conduct RF energy provided by generator 40 between tissue-contacting surfaces 112, 122 and through tissue grasped therebetween to treat, e.g., seal, tissue. Other suitable forms of energy, e.g., thermal, microwave, light, ultrasonic, etc., are also contemplated. Either or both jaw members 110, 120 may further include one or more non-conductive stop members 124 (FIG. 2A) disposed on the tissue-contacting surface 112, 122 thereof to define a minimum gap distance between tissue-contacting surfaces 112, 122 when jaw members 110, 120 are disposed in a fully approximated position.

An activation switch 30 is disposed on housing 20 and is coupled between generator 40 and tissue-contacting surfaces 112, 122 via wire 56c. Activation switch 30 is selectively activatable to provide energy from generator 40 to tissue-contacting surface 112 of jaw member 110 (and/or tissue-contacting surface 122 of jaw member 120) of end effector assembly 100. More specifically, when activation switch 30 is depressed, a resistance drop across circuitry 32 is recognized by generator 40 to initiate electrosurgical energy to supply a first electrical potential to jaw member 110 and a second electrical potential to jaw member 120.

End effector assembly 100 is designed as a bilateral assembly, i.e., wherein both jaw member 110 and jaw member 120 are movable about a pivot 19 relative to one another and to shaft 12. However, end effector assembly 100 may alternatively be configured as a unilateral assembly, i.e., wherein one of the jaw members, e.g., jaw member 120, is fixed relative to shaft 12 and the other jaw member, e.g., jaw member 110, is movable about pivot 19 relative to shaft 12 and the fixed jaw member 120.

In some embodiments, a knife assembly (not shown) is disposed within shaft 12 and a knife channel 115 is defined within one or both jaw members 110, 120 to permit reciprocation of a knife blade (not shown) therethrough, e.g., via actuation of trigger assembly 25, to cut tissue grasped between jaw members 110, 120. Alternatively or additionally, end effector assembly 100 may be configured for energy-based tissue cutting.

Figure 1B:
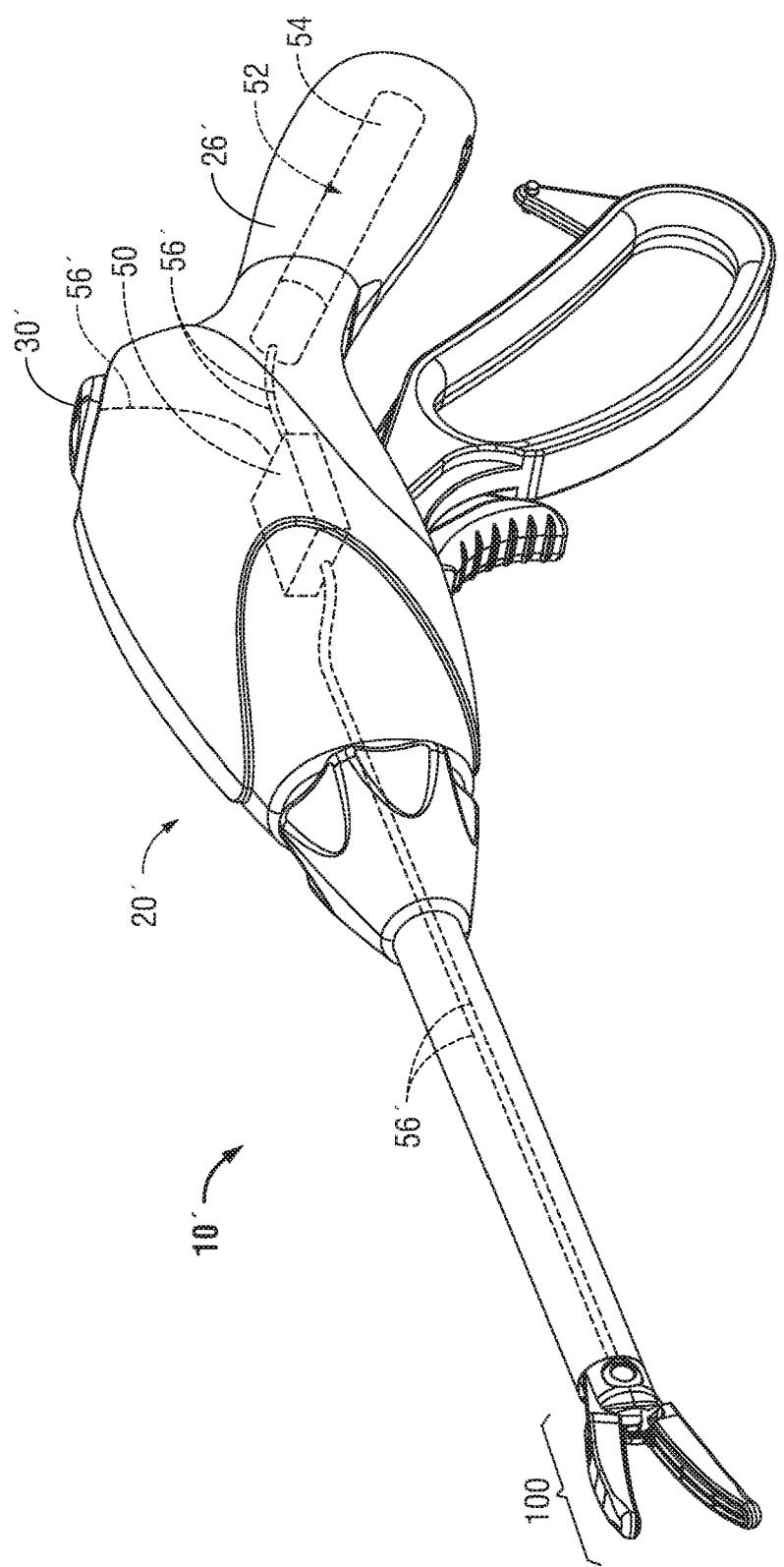
FIG. 1B is a perspective view of another surgical instrument provided in accordance with the present disclosure.

Referring to FIG. 1B, a cordless, or battery-powered forceps 10' is shown including an internal energy source 50, e.g., for generating RF energy or any other suitable form of energy (such as thermal, microwave, light, ultrasonic, etc.), disposed within housing 20'. Internal energy source 50 is operably coupled to a battery compartment 52 disposed within fixed handle 26' via one or more wires 56'. Battery compartment 52 is adapted to receive one or more batteries 54 for providing suitable energy to internal energy source 50. Internal energy source 50 provides RF energy to end effector assembly 100 via one or more wires 56' and is also coupled to activation switch 30' via one or more wires 56' for allowing the selective application of energy from internal energy source 50 to end effector assembly 100, similarly as detailed above. Forceps 10' may otherwise be configured similar to forceps 10 (FIG. 1A), discussed above.

Figure 2A:
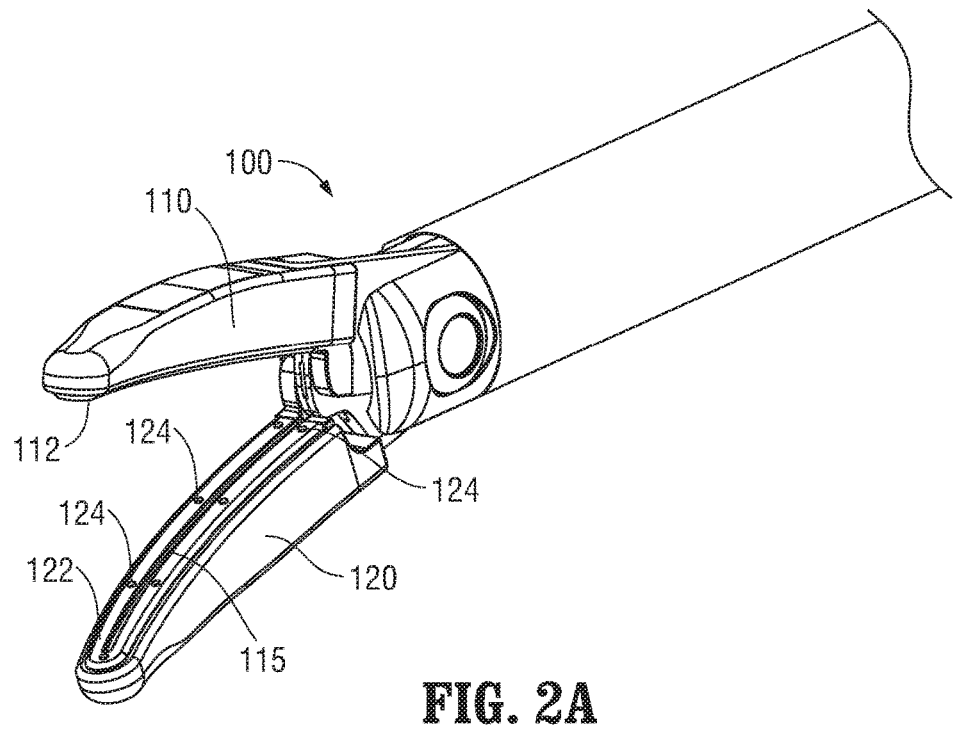
FIG. 2A is a perspective view of an end effector assembly provided in accordance with the present disclosure and configured for use with either of the surgical instruments of FIGS. 1A and 1B, wherein jaw members of the end effector assembly are disposed in a spaced-apart position.
Figure 2B:
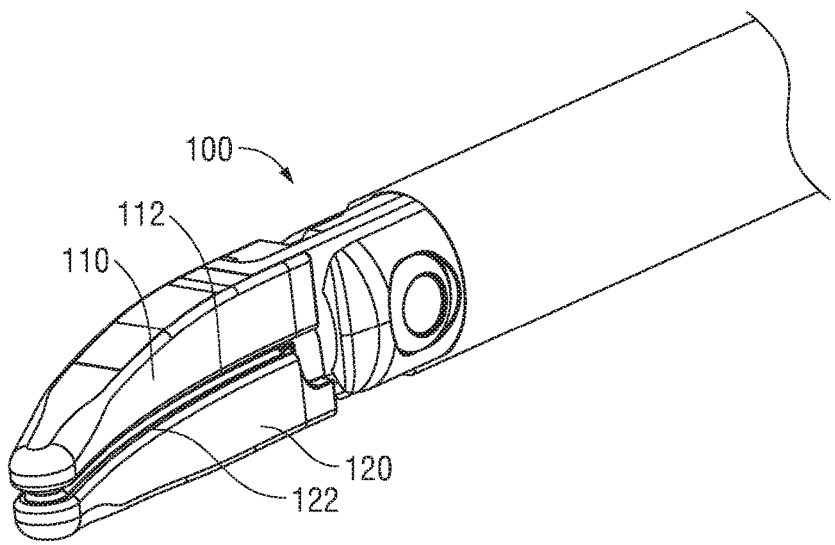
FIG. 2B is a perspective view of the end effector assembly of FIG. 2A, wherein the jaw members of the end effector assembly are disposed in an approximated position.

Turning now to FIGS. 2A-2B, in conjunction with FIG. 1A, an end effector assembly 100 configured for use with either forceps 10 (FIG. 1A), forceps 10' (FIG. 1B), or any other suitable surgical instrument is shown. End effector assembly 100, as mentioned above, includes a pair of opposing jaw members 110 and 120, each having an electrically-conductive tissue-contacting surface 112, 122, respectively, disposed thereon. Jaw members 110, 120 are movable between a spaced-apart position (FIG. 2A) and an approximated position (FIG. 2B) to grasp tissue between tissue-contacting surfaces 112, 122. When disposed in the approximated position (FIG. 2B), jaw members 110, 120 are configured to impart a specific clamping pressure (or clamping pressure within a specific clamping pressure range) to tissue grasped between jaw members 110, 120. More specifically, with additional reference to FIG. 1A, handle assembly 22 and/or latching assembly 27, in conjunction with the drive assembly (not shown), may be configured to impart the specific clamping pressure (or clamping pressure within a specific clamping pressure range) to tissue grasped between jaw members 110, 120. This may be achieved manually, e.g., via the user moving movable handle 24 from the initial position to a specific compressed position (or positions), via mechanical latching, e.g., wherein latch assembly 27 is configured to latch jaw members 110, 120 in a specific position (or positions), via feedback-based control (automatic or manual), or via any other suitable mechanism or feature. Suitable mechanisms for this purpose include those described in U.S. Pat. Nos. 5,776,130; 7,766,910; 7,771,426; and 8,226,650; and/or U.S. Patent Application Pub. Nos. 2009/0292283; 2012/0172873; and 2012/0184988, the entire contents of all of which are hereby incorporated by reference herein. Other suitable mechanisms for applying a specific clamping pressure (or clamping pressure within a specific clamping pressure range) to tissue grasped between jaw members 110, 120 may also be provided.

With tissue grasped between jaw members 110, 120 under the specific clamping pressure (or clamping pressure within a specific clamping pressure range), energy may be supplied to either or both tissue-contacting surfaces 112, 122 of jaw members 110, 120, respectively, to seal tissue. The particular sealing parameters provided in accordance with the present disclosure that have been found to be particularly applicable for use in sealing bowel tissue or other similar tissue structures are detailed below.

Figure 3:
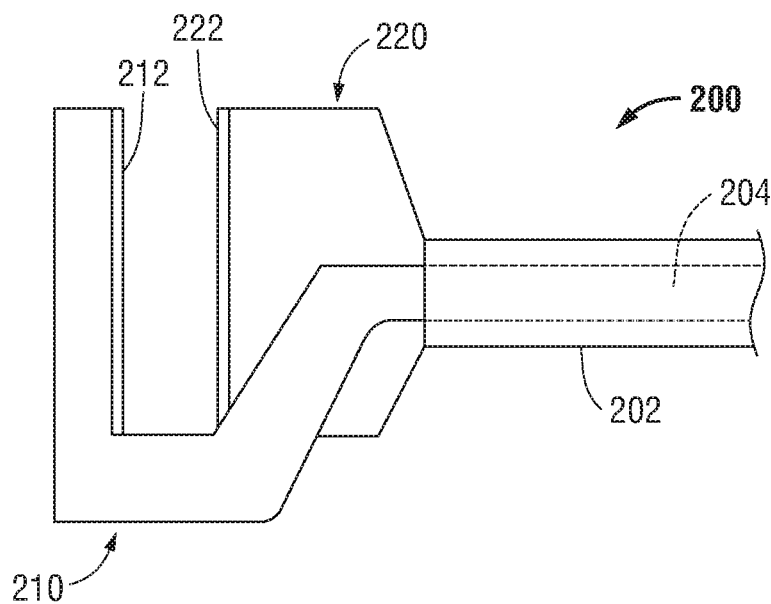
FIG. 3 is a side view of another end effector assembly provided in accordance with the present disclosure and configured for use with either of the surgical instruments of FIGS. 1A and 1B.

Turning now to FIG. 3, another embodiment of an end effector assembly configured for use with forceps 10 (FIG. 1A), forceps 10' (FIG. 1B), or any other suitable surgical instrument is shown and generally identified as end effector assembly 200. Similar to end effector assembly 100 (FIGS. 2A-2B), end effector assembly 200 includes first and second jaws members 210, 220, each including an opposed electrically-conductive tissue-contacting surface 212, 222 adapted to connect to a source of energy, e.g., generator 40 (FIG. 1A), for conducting energy between tissue-contacting surfaces 212, 222 and through tissue grasped therebetween to treat, e.g., seal, tissue. However, rather than providing pivotable jaw members, jaw members 210, 220 of end effector assembly 200 are linearly movable between a spaced-apart position and one or more approximated positions for grasping tissue therebetween. As shown, jaw member 210 is fixed relative to shaft 202, while jaw member 220 is coupled to a drive member 204 that is selectively translatable through and relative to shaft 202, e.g., via actuation of handle assembly 22 (FIG. 1A), to move jaw member 220 relative to jaw member 210 between the spaced-apart position and one or more approximated positions. Alternatively, end effector assembly 200 may be configured as a bilateral assembly, wherein both jaw members 210, 220 are movable relative to one another. In either configuration, tissue-contacting surfaces 212, 222 of jaw members 210, 220 are maintained in parallel orientation relative to one another regardless of the relative positioning therebetween, thus helping to ensure application of a uniform closure pressure to tissue grasped therebetween. Other suitable end effector assemblies configured to provide parallel closure of the tissue-contacting surfaces and suitable for use in accordance with the present disclosure include, for example, the end effector assemblies disclosed in U.S. Pat. No. 5,190,541 and U.S. Patent Application Pub. No. 2010/0057084, the entire contents of each of which is hereby incorporated by reference herein.

Figure 4:
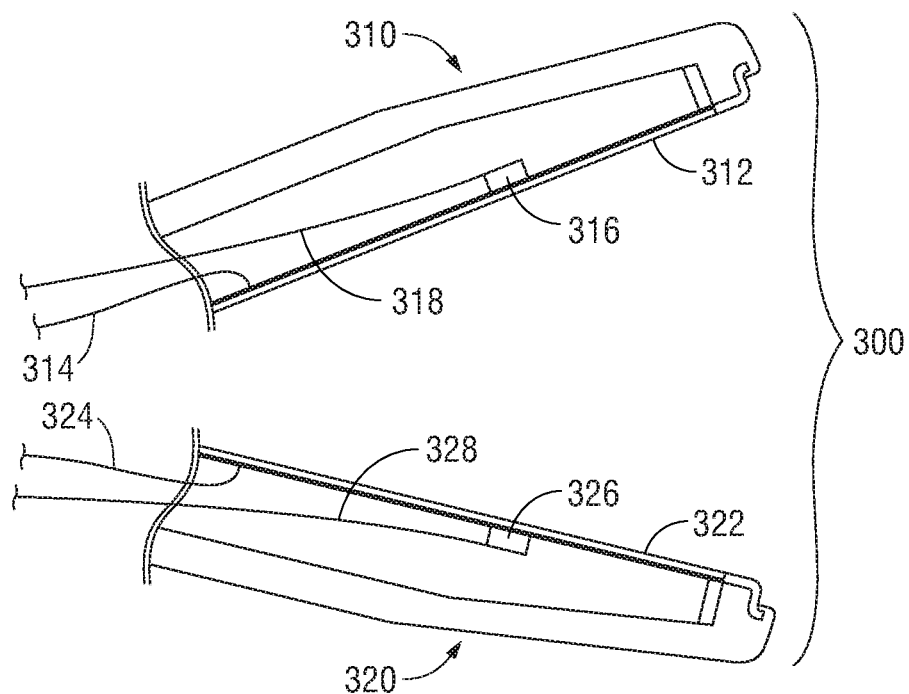
FIG. 4 is a longitudinal, cross-sectional view of the jaw members of another end effector assembly provided in accordance with the present disclosure.

FIG. 4 illustrates another end effector assembly provided in accordance with the present disclosure, shown generally identified by reference numeral 300. End effector assembly is similar to end effector assembly 100 (FIGS. 2A-2B) and may include any of the features of end effector assembly 100 (FIGS. 2A-2B) or any of the other end effector assemblies detailed herein, and vice versa. End effector assembly 300 includes first and second jaw members 310, 320 each including an electrically-conductive tissue-contacting surface 312, 322, respectively. Jaw members 310, 320 are movable between a spaced-apart position and one or more approximated positions to grasp tissue between tissue-contacting surfaces 312, 322. Wires 314, 324 electrically couple tissue-contacting surfaces 312, 322 to a source of energy, e.g., generator 400 (FIG. 5), for conducting RF energy between tissue-contacting surfaces 312, 322 and through tissue grasped therebetween to treat, e.g., seal, tissue.

Either or both jaw members 310, 320 of end effector assembly 300 may further include a sensor 316, 326 positioned adjacent the respective tissue-contacting surface 312, 322 and configured to sense one or more parameters, e.g., tissue impedance, tissue temperature, current and/or voltage applied to tissue, etc., and/or one or more tissue properties, e.g., optical tissue properties, physical tissue properties, etc. Sensors 316, 326 are coupled to the source of energy, e.g., generator 400 (FIG. 5), via wires 318, 328 to provide feedback and/or enable feedback-based control, as will be described in greater detail below.

Figure 5:
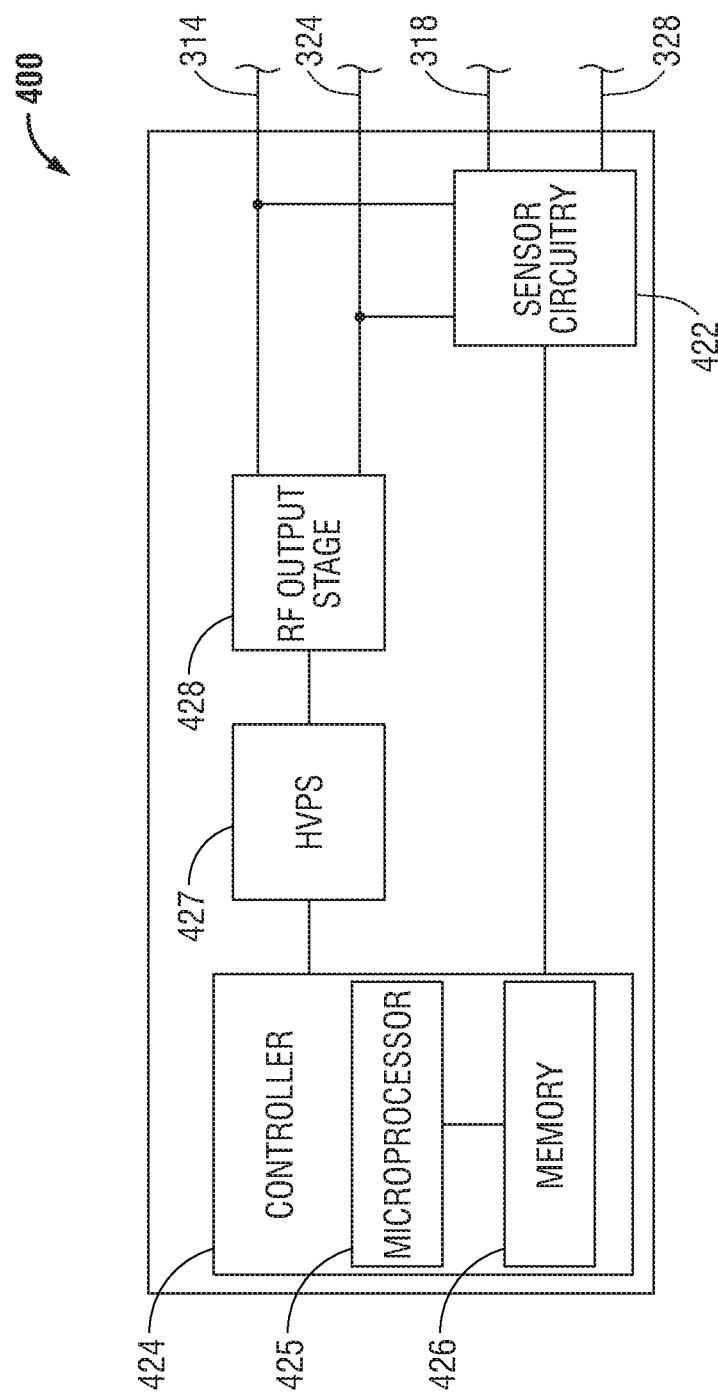
FIG. 5 is a schematic illustration of a generator provided in accordance with the present disclosure and configured for use with any of the end effector assemblies provided herein or any other suitable end effector assembly.

FIG. 5 shows a schematic block diagram of a generator 400 which may be utilized as a stand-alone generator, similar to generator 40 (FIG. 1), a generator incorporated into a surgical instrument, similar to generator 50 (FIG. 1B), or any other suitable generator. Generator 400 includes sensor circuitry 422, a controller 424, a high voltage DC power supply ("HVPS") 427 and an RF output stage 428. HVPS 427 provides high voltage DC power to RF output stage 428 which converts the high voltage DC power into RF energy for delivery to the end effector assembly, e.g., tissue-contacting surfaces 312, 322 of jaw members 310, 320, respectively, of end effector assembly 300 (FIG. 4). In particular, RF output stage 428 generates sinusoidal waveforms of high frequency RF energy. RF output stage 428 is configured to generate a plurality of waveforms having various duty cycles, peak voltages, crest factors, and other parameters, depending on a particular mode of operation.

Controller 424 includes a microprocessor 425 operably connected to a memory 426 which may be volatile type memory (e.g., RAM) and/or non-volatile type memory (e.g., flash media, disk media, etc.). Microprocessor 425 is operably connected to HVPS 427 and/or RF output stage 428 allowing microprocessor 425 to control the output of generator 400, e.g., in accordance with feedback received from sensor circuitry 422. Sensor circuitry 422 is operably coupled to wires 314, 324, which provide and return energy to/from tissue-contacting surfaces 312, 322 (FIG. 4), and/or wires 318, 328, which provide the sensed parameters from sensors 316, 326 of jaw members 310, 320 (see FIG. 4), to establish feedback control of the output of generator 400. From wires 314, 324, sensor circuitry 422 may determine one or more parameters, e.g., tissue impedance, output current and/or voltage, etc., while wires 318, 328 provide one or more of parameters or tissue properties, such as those noted above, or other suitable sensed parameters or tissue properties. Sensor circuitry 422 provides feedback based upon the sensed parameter(s) and/or tissue property(s) to controller 424 which, in turn, signals HVPS 427 and/or RF output stage 428 to adjust the DC and/or RF power supply accordingly.

With respect to controlling the output of generator 400 based upon tissue impedance, as mentioned above, tissue impedance can be monitored via sensor circuitry 22. More specifically, tissue impedance can be monitored relative to a target end impedance, e.g., the peak relative increase in impedance from a baseline value, while the monitored tissue impedances values can also be utilized to determine an impedance ramp, e.g., the rate of increase/decrease of tissue impedance as a function of time, as compared to a target impedance ramp. Depending on the particular target values set (and stored in memory 426, for example), microprocessor 425 may accordingly provide for automatic adjustment or control of the power and/or energy output of generator 400. A clock (not shown) may also be provided for controlling sealing time (the amount of time energy is supplied to tissue), in conjunction with the above-described impedance control. Impedance and/or sealing time control may be utilized to inhibit tissue denaturation, damage, tissue layer architecture breakdown, etc. A specific implementation of impedance feedback-based control particularly suited for sealing bowel tissue or other similar tissue structures is detailed below.

With respect to controlling the output of generator 400 based upon optical tissue properties, sensors 316, 318 (FIG. 4) may be configured as optical sensors configured to sense one or more optical properties of tissue and provide the same to sensor circuitry 422. Such optical sensors (or other suitable sensors) may be utilized to sense changes in the collagen matrix of tissue, denaturation of tissue, tissue damage, tissue layer architecture breakdown, and/or other suitable tissue properties. Microprocessor 425 may accordingly provide for automatic adjustment or control of the power and/or energy output of generator 400 based upon this sensed feedback, e.g., to inhibit denaturation, damage, tissue layer architecture breakdown, etc. Temperature-based feedback may additionally or alternatively be utilized to ensure tissue is sufficiently heated while also maintaining tissue at a temperature below the temperature at which denaturation, damage, tissue layer architecture breakdown, etc. occurs.

Any of the above-detailed end effector assemblies, instruments, and systems, may also be configured to work with robotic surgical systems and what is commonly referred to as "telesurgery." Such robotic systems employ various robotic elements to assist the surgeon in the operating theater and allow remote operation (or partial remote operation) of the end effector assembly and surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with surgical instrumentation and/or an end effector assembly, e.g., any of those disclosed hereinabove, while another surgeon (or group of surgeons) remotely controls the end effector assembly and/or other instrumentation via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce corresponding movement, manipulation, and/or actuation of the end effector assembly, e.g., to position the end effector assembly, grasp tissue, supply energy to tissue, deploy a knife for cutting tissue, release tissue, etc. The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. These sensors and feedback systems may be incorporated into and/or work in conjunction with the sensors and feedback systems of the instruments, end effector assemblies, and/or generators detailed hereinabove. The master handles may further include a variety of different actuators for delicate tissue manipulation or treatment to further enhancing the surgeon's ability to mimic actual operating conditions.

Sealing bowel tissue and other similar tissue structures has been found to require different sealing parameters, e.g., clamping pressure, gap distance, and/or energy control, as compared to sealing blood vessels, vascular tissue, and the like, due to differences in tissue composition and structure as well as differences in the physiological utilizations of these tissues. More specifically, bowel tissue is thicker and more muscular tissue as compared to blood vessels and vascular tissue. Bowel tissue is also more sensitive and is required to maintain function after sealing to fulfill its role in the digestive and excretory processes. As a result of the particular composition and functions of bowel tissue, a balance must be struck between the interest of ensuring formation of an adequate seal and the competing interest of minimizing denaturation, damage, tissue layer architecture breakdown, etc. of the tissue (which is typically not a concern with regard to sealing blood vessels and vascular tissues). It is contemplated that the above-described mechanisms, instruments, systems, end effector assemblies, generators, etc., alone or in combination with one another, be utilized to seal bowel tissue in accordance with these considerations, as described in detail below.

Taking into account the above-identified considerations, it has been found that a clamping pressure in the range of about 1 $kg/cm^2$ to about 2.5 $kg/cm^2$ applies sufficient pressure to bowel tissue to enable formation of an adequate bowel seal through merging of tissue layers, while also inhibiting/minimizing denaturation, damage, tissue layer architecture breakdown, etc. That is, bowel tissue seals have been found to be inadequate when formed using clamping pressures below about 1 kg/cm², while the level of tissue denaturation, damage, overall tissue layer architecture breakdown, etc. has been found to negatively effect the viability and/or performance of the sealed bowel tissue when formed using clamping pressures above 2.5 kg/cm². During sealing, the clamping pressure may be regulated and maintained within this clamping pressure range via use of any of the mechanisms detailed above or described in U.S. Pat. Nos. 5,776,130; 7,766,910; 7,771,426; and 8,226,650; and/or U.S. Patent Application Pub. Nos. 2009/0292283; 2012/0172873; and 2012/0184988, previously incorporated by reference herein, or via any other suitable methods or mechanisms.

With respect to gap distance, any suitable gap distance (constant or varied) between the tissue-contacting surfaces of the jaw members may be used during the sealing cycle so as to regulate and/or maintain the clamping pressure within the above-identified clamping pressure range throughout a portion of or the entire sealing cycle. The gap distance may likewise be maintained via use of any of the mechanisms detailed above or those described in U.S. Pat. Nos. 5,776,130; 7,766,910; 7,771,426; and 8,226,650; and/or U.S. Patent Application Pub. Nos. 2009/0292283; 2012/0172873; and 2012/0184988, previously incorporated by reference herein, or via any other suitable methods or mechanisms.

With respect to energy control, it has been found that an effective bowel seal, using a clamping pressure within the range of about 1 kg/cm² to about 2.5 kg/cm², can be established via temperature feedback-based energy control, optical tissue property feedback-based energy control, and/or impedance feedback-based energy control, e.g., using a feedback based system such as that detailed above with respect to end effector assembly 300 (FIG. 4) and generator 400 (FIG. 5).

Temperature control may be utilized to adjust the energy output such that tissue is sufficiently heated to enable formation of an effective tissue seal, but is maintained at a temperature below the temperature at which denaturation, damage, tissue layer architecture breakdown, etc. occurs.

Impedance control can be implemented to adjust the energy output using a target end impedance of about 200Ω and a target impedance ramp of about 0.010 Ω/ms, so as to ensure that the tissue is adequately sealed without damaging or negatively altering the tissue. Further, such impedance-control provides for a sealing cycle time typically in the range of about 18 to 22 seconds and, thus, tissue sealing time can also be utilized as feedback parameter.

Optical tissue property control may be utilized, as mentioned above, to adjust the energy output to inhibit denaturation, damage, breakdown of tissue layer architecture, etc. during the tissue sealing cycle by monitoring one or more properties or indications of such, e.g., changes in the collagen matrix of tissue, denaturation of tissue, changes in tissue layer architecture, etc.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system for sealing tissue, the system comprising:
   an energy-based surgical instrument including an end effector assembly having first and second jaw members, at least one of the first or second jaw members movable relative to the other between a spaced-apart position and an approximated position for grasping tissue therebetween, each of the first and second jaw members including an electrically-conductive surface, the end effector assembly further including at least one sensor operably associated therewith and configured to sense an impedance of the grasped tissue;
   a surgical generator including an energy output configured to supply energy to at least one of the electrically-conductive surfaces such that the energy is conducted between the electrically-conductive surfaces and through the grasped tissue, the surgical generator further including a microcontroller operably coupled to the at least one sensor and the energy output, the microcontroller configured to:
      monitor the impedance of the grasped tissue as a function of time during the supply of energy to the at least one electrically-conductive surface;
      determine an actual impedance ramp, wherein the actual impedance ramp represents the monitored impedance of the grasped tissue as a function of time;
      compare the actual impedance ramp with a target impedance ramp, wherein the target impedance ramp represents a change in impedance as a function of time that results in sealing of tissue while minimizing tissue denaturation, tissue damage, and breakdown of tissue layer architecture; and
      control the supply of energy from the energy output to the at least one of the electrically-conductive surfaces based on the comparison such that the grasped tissue is sealed with minimal tissue denaturation, tissue damage, and breakdown of tissue layer architecture of the grasped tissue that is being sealed to maintain viability of the tissue that is being sealed.

2. The system according to claim 1, wherein the target impedance ramp is about 0.010 Ω/ms.

3. The system according to claim 1, wherein the energy output of the surgical generator is configured to supply RF energy to the at least one electrically-conductive surface.

4. The system according to claim 3, wherein the energy output of the surgical generator is configured to supply RF energy to each of the electrically-conductive surfaces at different potentials such that energy is conducted therebetween and through the grasped tissue.

5. The system according to claim 1, wherein the microcontroller is further configured to stop the supply of energy from the energy output to the at least one electrically-conductive surface once a target end impedance is reached.

6. The system according to claim 5, wherein the target end impedance is about 200Ω.

7. A surgical system for sealing tissue, the system comprising:
   an energy-based surgical instrument including an end effector assembly having first and second jaw members, at least one of the first or second jaw members movable relative to the other between a spaced-apart position and an approximated position for grasping tissue therebetween, each of the first and second jaw members including an electrically-conductive surface, the end effector assembly further including at least one sensor operably associated therewith and configured to sense a temperature of the grasped tissue;

a surgical generator including an energy output configured to supply energy to at least one of the electrically-conductive surfaces such that the energy is conducted between the electrically-conductive surfaces and through the grasped tissue, the surgical generator further including a microcontroller operably coupled to the at least one sensor and the energy output, the microcontroller configured to:

monitor the temperature of the grasped tissue during the supply of energy from the energy output to the at least one electrically-conductive surface;

compare the temperature of the grasped tissue to a lower temperature limit, corresponding to a minimum temperature for sealing tissue, and an upper temperature limit, corresponding to a maximum temperature prior to occurrence of tissue denaturation, tissue damage, and breakdown of tissue layer architecture; and control the supply of energy from the energy output to the at least one electrically conductive surface to maintain the temperature of the grasped tissue between the lower temperature limit and the upper temperature limit such that the grasped tissue is sealed with minimal tissue denaturation, tissue damage, and breakdown of tissue layer architecture of the grasped tissue that is being sealed.

8. The system according to claim 7, wherein the energy output of the surgical generator is configured to supply RF energy to the at least one electrically-conductive surface.

9. The system according to claim 8, wherein the energy output of the surgical generator is configured to supply RF energy to each of the electrically-conductive surfaces at different potentials such that energy is conducted therebetween and through the grasped tissue.

* * * * *